(12) United States Patent
Dilley et al.

(10) Patent No.: US 10,064,943 B2
(45) Date of Patent: *Sep. 4, 2018

(54) THERAPEUTIC AND DIAGNOSTIC PROBES

(71) Applicant: LI-COR, INC., Lincoln, NE (US)

(72) Inventors: David L. Dilley, Lincoln, NE (US); Joy Kovar, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,247

(22) Filed: Jun. 2, 2015

(65) Prior Publication Data

US 2015/0343084 A1    Dec. 3, 2015

Related U.S. Application Data

(60) Provisional application No. 62/006,790, filed on Jun. 2, 2014, provisional application No. 62/017,165, filed on Jun. 25, 2014, provisional application No. 62/066,807, filed on Oct. 21, 2014, provisional application No. 62/082,052, filed on Nov. 19, 2014.

(51) Int. Cl.
*A61K 41/00* (2006.01)
*A61K 49/00* (2006.01)
*A61K 51/08* (2006.01)
*A61K 47/48* (2006.01)
*A61N 5/06* (2006.01)
*A61M 1/36* (2006.01)
*A61K 51/04* (2006.01)
*A61K 47/64* (2017.01)
*A61K 47/68* (2017.01)

(52) U.S. Cl.
CPC ...... *A61K 41/0071* (2013.01); *A61K 41/0009* (2013.01); *A61K 47/48246* (2013.01); *A61K 47/48269* (2013.01); *A61K 47/64* (2017.08); *A61K 47/642* (2017.08); *A61K 47/6415* (2017.08); *A61K 47/6849* (2017.08); *A61K 49/0032* (2013.01); *A61K 51/0446* (2013.01); *A61K 51/0497* (2013.01); *A61K 51/082* (2013.01); *A61K 51/083* (2013.01); *A61K 51/088* (2013.01); *A61M 1/3618* (2014.02); *A61M 1/3683* (2014.02); *A61M 1/3686* (2014.02); *A61N 5/062* (2013.01)

(58) Field of Classification Search
None
See application file for complete search history.

(56) References Cited

U.S. PATENT DOCUMENTS

| | | | |
|---|---|---|---|
| 6,995,274 B2 | 2/2006 | Lugade et al. | |
| 7,005,518 B2 | 2/2006 | Peng et al. | |
| 7,504,089 B2 | 3/2009 | Lugade et al. | |
| 7,597,878 B2 | 10/2009 | Kovar et al. | |
| 8,133,482 B2 | 3/2012 | Zheng et al. | |
| 8,227,621 B2 | 7/2012 | Peng et al. | |
| 8,303,936 B2 | 11/2012 | Draney et al. | |
| 8,524,239 B2 | 9/2013 | Kobayashi et al. | |
| 8,889,835 B2 | 11/2014 | Govindan et al. | |
| 9,358,306 B2 | 6/2016 | Bernardo et al. | |
| 2002/0114793 A1 | 8/2002 | Edelson et al. | |
| 2003/0139466 A1 | 7/2003 | Peritt et al. | |
| 2005/0112131 A1 | 5/2005 | Pogue et al. | |
| 2006/0134001 A1 | 6/2006 | Frangioni | |
| 2006/0204443 A1 | 9/2006 | Kobayashi et al. | |
| 2008/0081785 A1 | 4/2008 | Stewart et al. | |
| 2008/0193431 A1 | 8/2008 | Zheng et al. | |
| 2010/0135902 A1* | 6/2010 | Roberts | A61K 35/76 424/1.17 |
| 2010/0216226 A1 | 8/2010 | Hyde et al. | |
| 2012/0010557 A1 | 1/2012 | Heger | |
| 2012/0010558 A1* | 1/2012 | Kobayashi | A61K 41/0071 604/20 |
| 2013/0039860 A1 | 2/2013 | Cheung | |
| 2013/0116408 A1 | 5/2013 | De Los Pinos | |
| 2013/0131423 A1 | 5/2013 | Wang et al. | |
| 2013/0195760 A1 | 8/2013 | Olson | |
| 2013/0287688 A1 | 10/2013 | Jain et al. | |
| 2013/0302257 A1 | 11/2013 | Minko et al. | |
| 2013/0336995 A1 | 12/2013 | Kobayashi et al. | |
| 2014/0120119 A1 | 5/2014 | Kobayashi et al. | |
| 2014/0161725 A1 | 6/2014 | Morse et al. | |
| 2015/0343060 A1 | 12/2015 | Kovar et al. | |
| 2015/0374819 A1 | 12/2015 | Kovar | |
| 2016/0228568 A1 | 8/2016 | de los Pinos et al. | |

FOREIGN PATENT DOCUMENTS

| | | |
|---|---|---|
| GB | 1306627.9 | 4/2013 |
| WO | 2007/070680 A2 | 6/2007 |
| WO | 2008/005942 A2 | 1/2008 |
| WO | 2011123742 | 10/2011 |
| WO | 2012/078877 A2 | 6/2012 |
| WO | 2013/009475 A1 | 1/2013 |
| WO | 2015187677 | 12/2015 |

OTHER PUBLICATIONS

Reddy et al. Vascular targeted nanoparticles for imaging and treatment of brain tumors. 2006 Clin. Cancer Res. 12: 6677-6686.*

(Continued)

*Primary Examiner* — Michael G Hartley
*Assistant Examiner* — Jennifer Lamberski
(74) *Attorney, Agent, or Firm* — Kilpatrick Townsend and Stockton LLP

(57) ABSTRACT

The present invention provides compositions and methods of use of nanoparticle-based probes for in vivo imaging and therapy. The probes can be used to track diseased target cells by non-invasive imaging in the near-infrared range. Additionally, the probes can induce cell death of the target cells via photodynamic treatment.

9 Claims, 1 Drawing Sheet

(56) References Cited

OTHER PUBLICATIONS

Kircher et al. A multimodal nanoparticle for preoperative magnetic resonance imaging and intraoperative optical brain tumor delineation. 2003 Cancer Res. 63: 8122-8125.*

Rhee et al. Glycan-targeted virus-like nanoparticles for photodynamic therapy. 2012 Biomacromolecules 13: 2333-2338.*

Kovar et al, "A systematic approach to the development of fluorescent contrast agents for optical imaging of mouse cancer models," Analytical Biochemistry 367 (2007) 1-12.

Mitsunaga et al., "Cancer cell-selective in vivo near infrared photoimmunotherapy targeting specific membrane molecules," Nature Medicine, Dec. 2011, 17(12):1685-1691.

Peng et al., "Phthalocyanine dye as an extremely photostable and highly fluorescent near-infrared labeling reagent," Proceedings of SPIE, vol. 6097, E1-12., 2006.

Peng et al., "Quenched near-infrared fluorescent peptide substrate for HIV-1 protease assay," Proceedings of SPIE, vol. 6097, F1-12, 2006.

Kovar et al., Proc. of SPIE, vol. 7190 71900N-1 to 71900N-8, 2009.

Kovar et al., "A systematic approach to the development of fluorescent contrast agents for optical imaging of mouse cancer models", Anal Biochem. 367(1), Feb. 2, 2007, pp. 1-12.

Mitsuanga et al., "Near-infrared Theranostic Photoimmunotherapy (PIT): Repeated Exposure of Light Enhances the Effect of Immunoconjugate", Bioconjugate Chem, Feb. 27, 2012, pp. 604-609.

Galanzha et al., "In Vivo Magnetic Enrichment Photoacoustic Diagnosis and Photothermal Purging of Infected Blood Using Multifunctional Gold and Magnetic Nanoparticles", PLOS ONE, vol. 7 Issue 9 e45557, 2012, pp. 1-19.

Kovar et al., AACR-NCI-EORTC International Conference: Molecular Targets and Cancer Therapeutics, San Francisco, California, Nov. 12-16, 2011, Abstract.

* cited by examiner

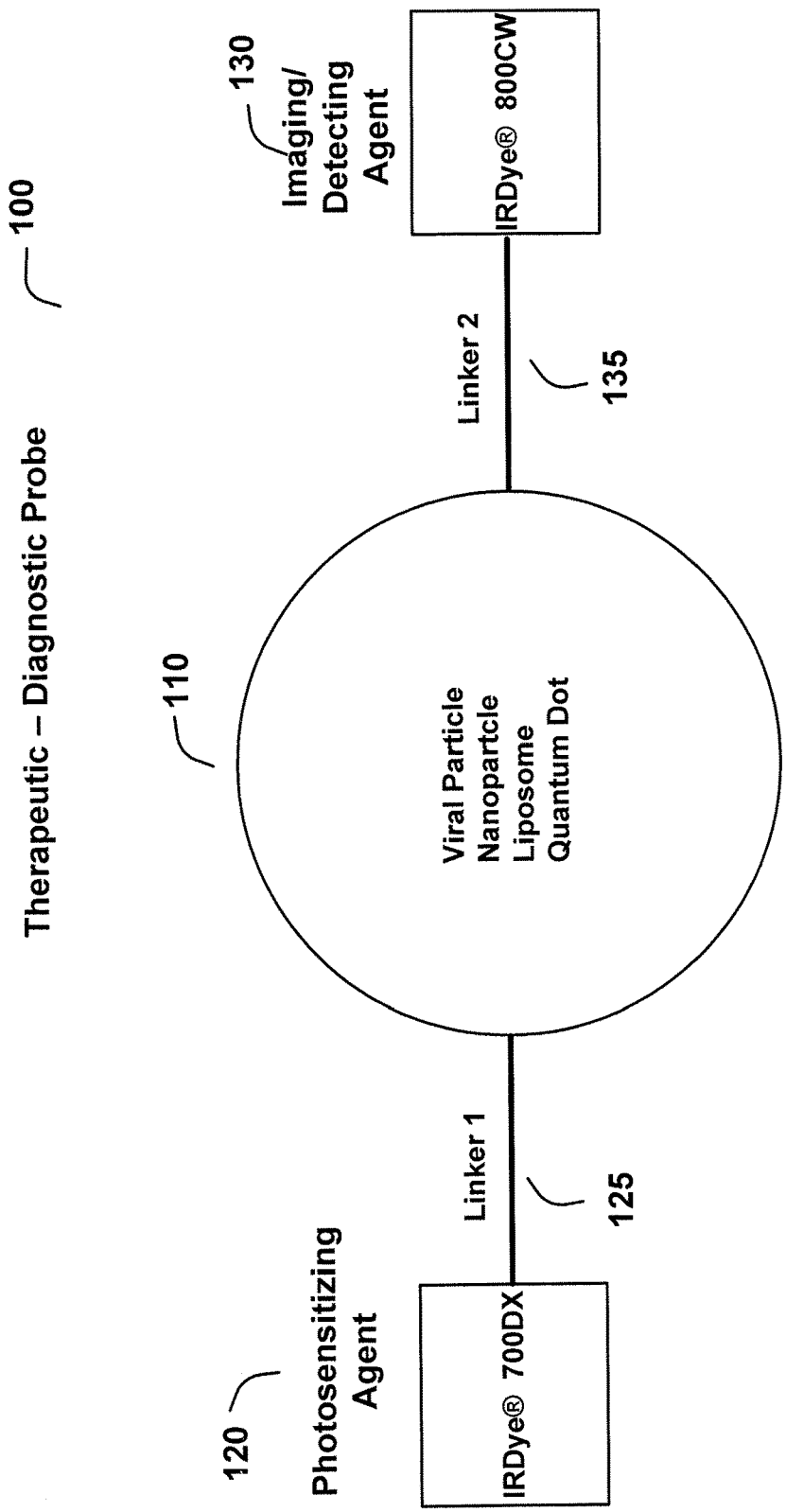

THERAPEUTIC AND DIAGNOSTIC PROBES

CROSS-REFERENCE TO RELATED APPLICATIONS

This application claims priority to U.S. Provisional Patent Application Nos. 62/006,790, filed Jun. 2, 2014; 62/017,165, filed Jun. 25, 2014; 62/066,807, filed Oct. 21, 2014 and 62/082,052, filed Nov. 19, 2014, the teachings all of which are hereby incorporated by reference in their entireties for all purposes.

BACKGROUND OF THE INVENTION

Photodynamic therapy (PDT) is a clinically approved and rapidly evolving treatment regimen for disease including cancer, cardiovascular disease, dermatological diseases and ophthalmic disease. PDT traditionally involves administration of a photosensitizer that preferentially accumulates within a target tissue site. Following illumination of the tissue site with light of an appropriate wavelength, in the presence of molecular oxygen, reactive oxygen species, such as singlet oxygen, free radicals and peroxides are produced which, in turn, damage cellular structures containing the photo-sensitizer. The effects are localized to the vicinity of the target tissue and within a few millimeters of the light source, which minimizes systemic and normal tissue toxicity.

Both disease treatment and detection depend on the selective delivery of appropriate agents to the affected tissue site. Current photodynamic therapeutic agents lack effective tissue localization. There remains a need for compositions and methods to detect and treat target cells and/or tissues in a non-invasive manner. The present invention satisfies these and other needs.

BRIEF SUMMARY OF THE INVENTION

In one aspect, provided herein is a probe comprising a nanocarrier attached to an imaging agent and a therapeutic agent. In some embodiments, the nanocarrier is selected from a group of a virus-like particle, a nanoparticle, a liposome, a quantum dot, or a combination thereof. In some instances, the nanoparticle is selected from the group consisting of a gold nanoparticle, a magnetic nanoparticle, a polymeric nanoparticle, a carbon nanotube, an inorganic nanoparticle, or a combination thereof.

In certain instances, the probe is a nanocarrier comprising both an imaging agent and a therapeutic agent. In other instances, the present invention provides a composition comprising two probes, wherein the first probe is a nanocarrier with an imaging agent and a second probe is a nanocarrier comprising a therapeutic agent.

In certain instances, the present invention provides methods for treatment, wherein for example, a tumor is treated using the therapeutic agent and thereafter, imaged to ascertain the extent of treatment. The treatment can be repeated until the tumor is destroyed or the site of treatment is satisfactorily complete. In certain instances, the methods include, injecting the probe or composition, treating the tumor using photodynamic therapy and thereafter imaging to ascertain the extent of treatment.

In some embodiments, the virus-like particle comprises a L1 capsid protein, a L2 capsid protein, or a combination thereof. In some instances, the ratio of L1:L2 capsid protein is about 15:1. In other instances, the ratio of L1:L2 capsid protein is about 10:1. In yet other instances, the ratio of L1:L2 capsid protein is about 5:1.

In some embodiments, the nanocarrier further comprises a targeting agent. In some instances, the targeting agent is an antibody or fragment thereof, a nanobody, an Affibody®, a diabody, a minibody, an antigen, a ligand, a protein, a peptide, a nucleic acid or a small molecule.

In some embodiments, the therapeutic agent is attached to the nanocarrier via a first linker. In some embodiments, the imaging agent is attached to the nanocarrier via a second linker.

In some embodiments, the therapeutic agent is a photosensitizer. In some instances, the photosensitizer is IRDye® 700DX. In some embodiments, the imaging agent is a cyanine dye. In some instances, the cyanine dye is IRDye® 800CW.

In another aspect, provided herein is a method for detecting a target cell in an individual. The method comprises (a) contacting the target cell with a probe comprising a nanocarrier attached to an imaging agent and a therapeutic agent, wherein the probe selectively associates with the target cell; and (b) detecting the imaging agent thereby providing an indication of the presence and/or location of the target cell in the individual. In some instances, the step of contacting comprises systemic administration to a subject, local administration to a target site, or administration to a surgical site. In some embodiments, the method further comprises exposing the therapeutic agent to a photoactivating light, thereby inducing apoptosis and/or necrosis of the target cell.

In some embodiments, the imaging agent is a cyanine dye. In some instances, the cyanine dye is IRDye® 800CW.

In some embodiments, the target cell is a cell of a solid tumor. In other embodiments, the target cell is a circulating tumor cell.

In another aspect, provided herein is a method for inducing cell death in a target cell in an individual. The method comprises (a) contacting the cell with a probe comprising a nanocarrier attached to an imaging agent and a therapeutic agent, wherein the probe selectively associates with the target cell; and (b) exposing said therapeutic agent to a photoactivating light, thereby inducing apoptosis and/or necrosis of the target cell in the individual. In some instances, the step of contacting comprises systemic administration to a subject, local administration to a target site, or administration to a surgical site. In some embodiments, the method further comprises detecting the imaging agent thereby providing an indication of the presence and/or location of the target cell in the individual.

In some embodiments, the therapeutic agent is a photosensitizer. In some instances, the photosensitizer is IRDye® 700DX.

In some embodiments, the target cell is a cell of a solid tumor. In other embodiments, the target cell is a circulating tumor cell.

Other objects, features, and advantages of the present invention will be apparent to one of skill in the art from the following detailed description and figures.

BRIEF DESCRIPTION OF THE DRAWING

The FIGURE provides an exemplary embodiment of the therapeutic-diagnostic probe 100 described herein. A nanocarrier 110 is attached to a photosensitizing agent 120 through a first linker 125. The nanocarriers is also attached to an imaging and/or detecting agent 130 through a second linker 135.

DETAILED DESCRIPTION OF THE INVENTION

I. Introduction

The present invention provides a method of photodynamically treating a target site of an individual, e.g., a human. The method includes the step of administering a therapeutic-diagnostic probe comprising a nanocarrier, a detecting agent and a photosensitizing agent to the individual. Once the probe has been administered, the tissue site is treated with a photoactivating light. Photons from the light are absorbed by the photosensitizing agent which activates oxygen in the site to produce reactive oxygen species that results in death of the target cells within the tissue site. The location of the probe can be determined by detecting the imaging agent. Compositions of the probe are also provided herein.

In certain instances, the therapeutic and diagnostic portions can be separate components. In such cases, a diagnostic probe delivery can be conducted either before or after the therapy component.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "capsid" is meant to refer to the protein shell of the virus. In particular embodiments, the capsid refers to the protein shell of the papillomavirus or adenovirus. A viral capsid may consist of multimers of oligomeric protein subunits. In certain embodiments, the capsid comprises the papillomavirus L1 and L2 proteins.

The term "targeting agent" refers generally to a molecule or compound that binds to a particular target molecule and forms a bound complex. The binding can be highly specific binding. For example, the targeting agent and its corresponding target molecule can form a specific binding pair. Examples include, but are not limited to small organic molecules, sugars, lectins, nucleic acids, proteins, peptides, antibodies, nanobodies, Affibodies®, diabodies, minibodies, antigens, ligands, cytokines, receptor proteins, growth factors, nucleic acid binding proteins, small molecules, and the like which specifically bind desired target molecules, target collections of molecules, target receptors, target cells, and the like.

The term "nanoparticle" refers to a particle having a sub-micron (μm) size. In various embodiments, microparticles have a characteristic size (e.g., diameter) less than about 1 μm, 800 nm, or 500 nm, preferably less than about 400 nm, 300 nm, or 200 nm, more preferably about 100 nm or less, about 50 nm or less or about 30 or 20 nm or less.

The term "linker" refers to the atoms joining the agent (e.g., imaging agent, therapeutic agent, and targeting agent) to the nanocarrier or biomolecule.

III. Detailed Descriptions of Embodiments

In some embodiments, the present invention pertains to nanocarrier-based probes that are useful as diagnostic agents and/or therapeutics. In some instances, the probes can be utilized to simultaneously image and treat diseased cells and tissues.

A. Nanocarriers

The therapeutic-diagnostic probes of the present invention comprise a nanocarrier, such as a virus-like particle, a nanoparticle, a liposome, a quantum dot, or a combination thereof, that is attached to a detecting agent and a photosensitizing agent. The nanocarrier can be directed to the target cell or tissue of interest by passive targeting or directed targeting. With passive targeting the probe is transported to the target by convection (e.g., movement within fluids) or passive diffusion (e.g., movement across the cell membrane according to, for example, a concentration gradient or without the use of cellular energy) within the body. For directed targeting, a targeting agent is attached to the surface of the nanocarrier for binding to its corresponding binding partner expressed at the target site.

1. Virus-Like Particles

Provided herein are virus-like particles that can be used for delivering imaging agents and therapeutics (e.g., photodynamic therapy) to cells and tissues of the body. These particles can be produced from recombinant proteins that mimic specific viruses. The particles can be loaded with imaging agents and photosensitizing agents and targeted to specific cells. For instance, the virus-like particles can deliver the agents to tumor cells, such as tumor cells from the lung, colon, ovary, kidney, skin, central nervous system, blood, prostate, breast and the like.

Viron-derived nanocarriers can be produced from papillomavirus capsids composed of L1 (major capsid protein) and L2 capsid (minor capsid protein) proteins. The viral-like particles of the present invention can be formed from about multiple assembled capsomers wherein each capsomer comprises L1 and L2 capsid proteins. The particles can have a stochiometry of L1:L2 of about 15:1, about 10:1, or about 5:1. In other instances, the ratio is 15:1, 14:1, 13:1, 12:1, 11:1, 10:1, 9:1, 8:1, 7:1, 6:1, 5:1, 4:1, 3:1, 2:1, or 1:1.

In some embodiments, the papillomavirus is from a non-human vertebrates such as, but not limited to, an ungulate, canine, lapine, avian, rodent, simian, marsupial or marine mammal. In some embodiments, the papillomavirus is from a human. In other embodiments, the papillomavirus is selected from HPV-1, HPV-2, HPV-5, HPV-6, HPV-11, HPV-18, HPV-31, HPV-45, HPV-52, and HPV-58, bovine papillomavirus-1, bovine papillomavirus-2, bovine papillomavirus-4, cottontail rabbit papillomavirus, and rhesus macaque papillomavirus.

In some embodiments, the agent, such as an imaging agent or a therapeutic agent, is encapsulated within the virus-like particle.

The virus-like particle can be generated by isolating and purifying capsid proteins produced in a host cell system, such as bacterial cell, yeast cell, insect cell or mammalian cell system. In some embodiments, the L1 and L2 proteins are intracellularly assembled. Alternatively, the particle can be generated by purifying the capsid proteins produced in an in vitro cell-free protein synthesis system. The capsid proteins can readily self-assemble into particles. For instance, L1 can spontaneously self-assemble into a 60 nm, 72-pentamer icosahedral structure that closely resembles a papillomavirus virion.

In some embodiments, viral capsid proteins L1 and/or L2 or fragments thereof (e.g., L1 peptides and/or L2 peptides) are coupled to a nanocarrier. In some instances, the peptide is coupled to the external surface of the nanocarrier covalently or non-covalently. In some instances, the coupling comprises a covalent linker such as, but not limited to, an amide linker, a disulfide linker, a thioether linker, a hydrazone linker, a hydrazide linker, an imine or oxime linker, an urea or thiourea linker, an amidine linker, an amine linker, or a sulfonamide linker.

2. Polymeric Nanoparticles

Biodegradable or non-biodegradable polymers may be used to form nanoparticles of the present invention. In certain embodiments, synthetic polymers are used, although natural polymers may be used and may have equivalent or even better properties, especially some of the natural biopolymers which degrade by hydrolysis, such as some of the polyhydroxyalkanoates. Examples of synthetic polymers include, but are not limited to, poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, celluklose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt, polymers of acrylic acid, methacrylic acid or copolymers or derivatives thereof including esters, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(butyric acid), poly(valeric acid), and poly(lactide-co-caprolactone), cyclodextrins, and copolymers and blends thereof. As used herein, the term "derivatives" includes polymers having substitutions, additions of chemical groups and other modifications routinely made by those skilled in the art.

In particular embodiments, PLGA is used as the biodegradable polymer. Examples of biodegradable polymers useful in the present invention include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), and blends and copolymers thereof. Natural polymers include, but are not limited to, proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). Examples of non-biodegradable polymers include, but are not limited to, ethylene vinyl acetate, poly(meth)acrylic acid, polyamides, or copolymers or mixtures thereof.

B. Liposomes

Liposomes are artificial vesicles composed of concentric lipid bilayers separated by water-compartments and have been extensively investigated as drug delivery vehicles. Due to their structure, chemical composition and colloidal size, all of which can be well controlled by preparation methods, liposomes exhibit colloidal size, i.e., rather uniform particle size distributions in the range from 10 nm to 10 µm, and useful membrane and surface characteristics. Liposomes can deliver therapeutics to diseased tissues, for example, in circulation, and also rapidly enter the liver, spleen, kidneys and reticuloendothelial systems.

In some embodiments, the liposome comprises synthetic phospholipids such as, but not limited to, phosphatidyl cholines, e.g., dipalmitoylphosphatidy choline (DPPC), dimyristoyl phosphatidyl choline (DMPC), and distearoyl phosphatidyl choline (DSPC), and phosphatidyl glycerols, e.g., as dipalmitoyl glycerol (DPPG) or dimyristoyl phosphatidyl glycerol (DMPG). The liposome can also include a monosaccharide such as glucose or fructose. In some embodiments, the phospholipids are conjugated to a polyethylene glycol (PEG) molecule.

C. Quantum Dots

Quantum dots are small molecular clusters having up to about a few hundred atoms. Quantum dots can have a size range of about 1 nm to about 20 nm in diameter. They are typically only a few nanometers in size. A quantum dot is typically composed of a semiconductor material or materials, metal(s), or metal oxides exhibiting a certain energy. A variety of materials may be utilized for construction of nanoparticles, including, but not limited to, $TiO_2$, $Al_2O_3$, AgBr, CdSe, CdS, CdSlSel, CuCl, $CdTe_xS_{1-x}$, ZnTe, ZnSe, ZnS, GaN, InGaN, InP, CdS/HgS/CdS, InAs/GaAs, Group II-VI, Groups III-V, and Groups I-VII semiconductors as well as Group IV metals and alloys. A quantum dot may also be surrounded by a material or materials having wider bandgap energies (for example, ZnS-capped CdS), and especially may be surrounded by those materials that improve biocompatibility of the nanoparticles.

Quantum dots can photoluminesce when stimulated by light having a wavelength in which the energy of a photon is at least equal to the energy of the light-emitting material forming the quantum dot. Consequently, quantum dots absorb light of a first wavelength and emit light at a second wavelength that is shorter than the first wavelength. The pump light supplied by, e.g., a laser or light-emitting diode ("LED") array or other light source in which photons have an energy at least equal to the band-gap energy of the quantum dot is therefore absorbed by the quantum dot. The quantum dot re-emits energy in the form of light at a different wavelength and in a multidirectional fashion.

There are a number of methods of making quantum dots. The synthesis of small semiconductor clusters in trioctylphosphine oxide (TOPO) at 300° C. has been shown to yield highly fluorescent (quantum yields >50%) small particles of a number of semiconductor materials, such as CdSe, InP and InAs. Growth conditions such as the length of time of crystallization, concentration of monomer, and temperature establish the size of the quantum dot and therefore the color of the light emitted from the quantum dot. (See, Green and O'Brien, *Chem. Commun.*, 1999, 2235-41; and U.S. Pat. Nos. 5,909,670, 5,943,354, and 5,882,779). Quantum dots are commercially available from manufacturers such as Life Technologies, Nanoco Technologies, and Sigma-Aldrich.

In some embodiments, the nanoparticle comprises an inorganic material and/or a quantum dot. In some instances, the nanoparticle includes one or more materials selected from the group consisting of cadmium, zinc, magnesium, mercury, aluminum, gallium, indium, and thallium. Optionally, the nanoparticle can contain one or more materials selected from the group of cadmium, zinc, magnesium, mercury, aluminum, gallium, indium, or thallium.

In particular embodiments, the nanoparticle comprising an inorganic material can comprises a core and a shell, where the shell comprises a semiconductor overcoating the core. In certain embodiments the shell comprises a group II, III, IV, V, or VI semiconductor. In particular embodiments the shell comprises one or more materials selected from the group consisting of ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, and TlSb. In certain embodiments the nanoparticle comprises a CdSe core and a ZnS shell and a $SiO_2$ hydrophilic coating.

D. Imaging Agents

The compositions and methods described herein are useful for non-invasive imaging in the near-infrared spectral range. In some embodiments, the imaging agent can be a detecting agent. In some embodiments, the imaging agent for the probe of the present invention is a cyanine dye. In preferred embodiments, the cyanine dye is IRDye® 800CW or an equivalent thereof. Detailed description of other useful cyanine dyes are found in, for example, U.S. Pat. Nos. 6,995,274; 7,597,878, 7,504,089; and 8,303,939, the disclosures are hereby incorporated by reference in their entirety for all purposes.

The imaging and/or detecting agent can be directly attached to the nanocarriers described herein. In some embodiments, the agent is attached to a biomolecule, including, but not limited to, a viral particle, a nanoparticle, a liposome, a quantum dot, a protein, a peptide, a ligand, an enzyme substrate, a hormone, an antibody, an antigen, a hapten, an avidin, a streptavidin, a carbohydrate, an oligosaccharide, a polysaccharide, an oligosaccharide, a nucleic acid, a deoxy nucleic acid, a fragment of DNA, a fragment of RNA, nucleotide triphosphates, acyclo terminator triphosphates, or PNA In other embodiments, the biomolecule is a ligand that has an affinity for a receptor expressed by a cell or tissue of interest. In some instances, the receptor is selected from the group consisting of EGFR, HER2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocorticosteroid receptor, retinoid-X receptor, RHAMM, high affinity folate receptors, Met receptor, estrogen receptor and Ki67.

In yet other embodiments, the biomolecule is selected from the group of somatostatin, endostatin, a carbohydrate, a monosaccharide, a disaccharide, a trisaccharide, an oligosaccharide, aptamer, liposome and PEG. Alternatively, the biomolecule is 2-deoxy-D-glucose, 2-deoxy-D-glucosamine, a glucose derivative, glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, or tagatose.

In still other embodiments, the biomolecule is selected from the group of angiopoietins, angiostatin, angiotensin II, $\alpha_2$-antiplasmin, annexin V, β-cyclodextrin tetradecasulfate, endoglin, endosialin, endostatin, epidermal growth factor, fibrin, fibrinopeptide β, fibroblast growth factor, FGF-3, basic fibronectin, fumagillin heparin, hepatocyte growth factor, hyaluronan, insulin-like growth factor, interferon-α, β inhibitors, IL inhibitor, laminin, leukemia inhibitory factor, linomide, matrix metalloproteinase-2, metalloproteinases, metalloproteinase inhibitors, antibodies or fragments, monoclonal antibodies or fragments, cyclic $RGD_D$ FV, placental growth factor, placental proliferin-related protein, plasminogen, plasminogen activator, plasminogen activator inhibitor-1, platelet activating factor antagonists, platelet-derived growth factor, platelet-derived growth factor receptors, platelet-derived endothelial cell growth factor, pleiotropin, proliferin, proliferin-related protein, selectins: E-selectin, SPARC, snake venoms, substance P, suramin, tissue inhibitor of metalloproteinases, thalidomide, thrombin, thrombin-receptor-activating tetradecapeptide, transforming growth factor-α, β, transforming growth factor receptor, tumor growth factor-α, tumor necrosis factor, vitronectin, avidin or streptavidin.

In some embodiments, the probes of the present invention are used to directly label a cell or tissue so that the cell or tissue can be identified or quantitated. For instance, such probes can be added as part of a detection assay for a target cell or tissue, as a detectable tracer element in a biological or non-biological fluid; or for such purposes as photodynamic therapy of diseased tissues, in which a dyed cell is irradiated to selectively destroy the diseased cells, usually through the photosensitized production of singlet oxygen.

E. Photosensitizing Agents

In some embodiments, the photosensitizing agent of the probe is a phthalocyanine dye. In some instances, the phthalocyanine dye comprises a luminescent fluorophore moiety having at least one silicon containing aqueous-solubilizing moiety, wherein the phthalocyanine dye has a core atom selected from Si, Ge, Sn, and Al. Preferably, the phthalocyanine dye exists as a single core isomer, essentially free of other isomers and has a reactive or activatible group. The core atom is preferably Si. In preferred embodiments, the phthalocyanine dye is IRDye® 700DX or an equivalent thereof. Detailed description of phthalocyanine dyes are found in, for example, U.S. Pat. No. 7,005,518, the disclosure is herein incorporated by reference in its entirety for all purposes.

The term "IRDye® 700® DX" or "IR700" refers to a dye having the preferred NHS ester linkage to allow for conjugation. Typically, the nanocarrier, agent or biomolecule has a primary amine (e.g., an amino group) wherein the NHS ester and the amino group react to form an amide bond, linking the targeting moiety such as an antibody to 700DX. The NHS ester IRDye® 700DX has the following formula:

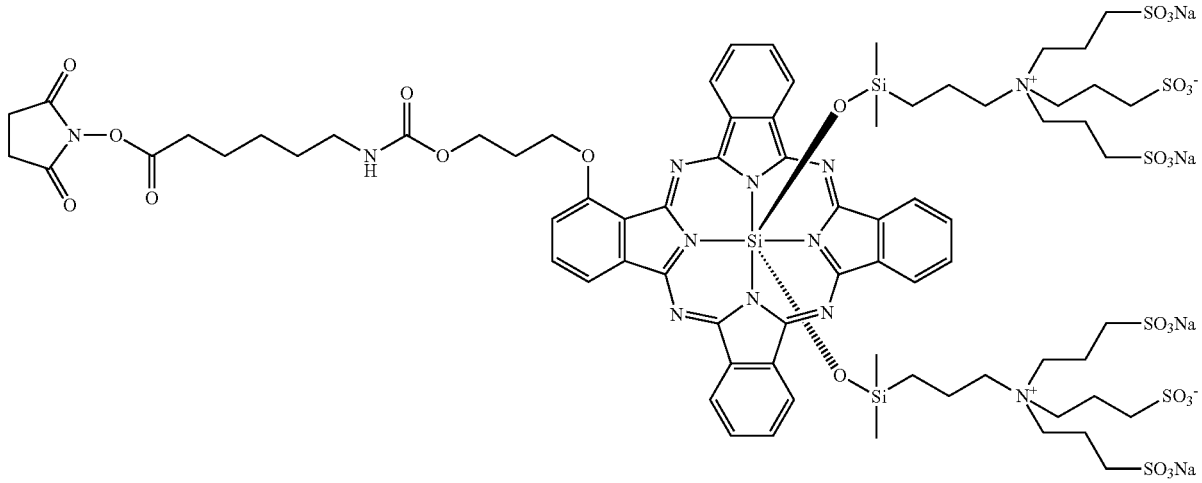

The dye is commercially available from LI-COR (Lincoln, Nebr.). Amino-reactive IRDye® 700DX is a relatively hydrophilic dye and can be covalently conjugated with an antibody using the NHS ester of IRDye® 700DX. Other variations of IRDye 700Dx are disclosed in U.S. Pat. No. 7,005,518 (incorporated herein by reference), and those too are useful in the present invention. The carboxylate derivative has the following name and structure, silicate(5-), bis[N-[3-[(hydroxy-.kappa.O)dimethylsilyl]propyl]-3-sulfo-N,N-bis(3-sulfopropyl)-1-propanaminiumato(4-)][6-[[[3-[(29H,31H-phthalocyanin-yl-.kappa.N29,.kappa.N30,.kappa.N31,.kappa.N32)oxy]propoxy]carbonyl]amino] hexanoato(3-)]-, sodium (1:5); CAS Registry Number: [1623074-46-3]:

an ether, an oxime, a phosphate ester, a sulfonamide, a thioether, a thiourea, or a urea. Preferably, the bond is covalent, such as an amide or carbamate bond. Non-limiting examples of reactive functionalities useful for attaching the dye to the biomolecule are described in, for example, U.S. Pat. No. 7,005,518.

F. Linkers

The detecting agent and/or photosensitizing agent can be attached to the nanocarrier or a biomolecule of the nanocarriers via a linker. In some embodiments, the linker is a direct link or a covalent linkage, wherein the covalent linkage is linear or branched, cyclic or heterocyclic, saturated or unsaturated, having 1-60 atoms selected from the group consisting of C, N, P, O, and S, wherein the linker can

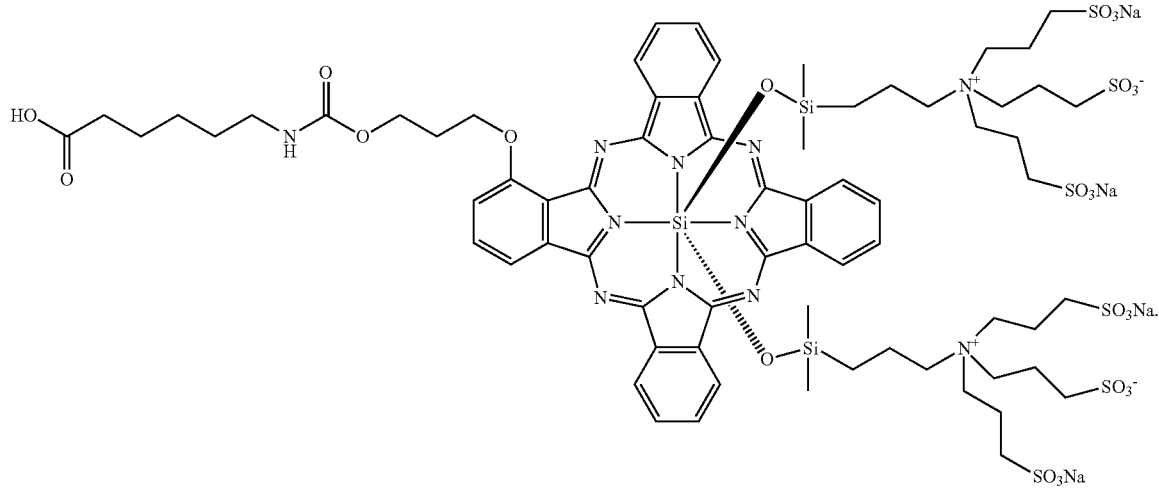

The photosensitizing agent can be directly attached to the nanocarriers described herein. In some embodiments, the agent is attached to a biomolecule, including, but not limited to, a viral particle, a nanoparticle, a liposome, a quantum dot, a small molecule, a cell, a drug (e.g., small molecule), a liposome, a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, peptide nucleic acid (PNA) biomolecules, or a combination thereof. The photosensitizing agent can be linked to a material, such as a biomolecule, for example, by using phosphoramidite chemistry, ultimately forming a phosphate linkage between the dye and the biomolecule. For examples of such labeling methods, see U.S. Pat. No. 6,027,709, which discloses many preferred linking groups, linking methods, and biomolecules that can be readily labeled. Many methods of linking dyes to various types of biomolecules are well known in the art. For a thorough review of oligonucleotide labeling procedures, see, e.g., R. Haugland in *Excited States of Biopolymers*, Steiner ed., Plenum Press (1983), *Fluorogenic Probe Design and Synthesis: A Technical Guide*, PE Applied Biosystems (1996), and G. T. Herman, *Bioconjugate Techniques*, Academic Press (1996).

In some embodiments, the photosensitizing agent is reacted with a biomolecule to form a covalent bond between the dye and the biomolecule. The bond is for example, an amide, a secondary or tertiary amine, a carbamate, an ester, have additional hydrogen atoms to fill valences, and wherein the linker contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds. The linker can include phosphoramidite groups, NHS ester, activated carboxylic acid, thiocyanate, isothiocyanate, maleimide and iodoacetamide. The linker may comprise a terminal amino, carboxylic acid, or sulfhydryl group covalently attached to the ring. In certain instances, the terminal amino, carboxylic acid, or sulfhydryl group is shown and is represented as -L-NH$_2$, or -L-C(O)OH or -L-SH.

In certain embodiments, the linker arm is —(CH$_2$)$_n$—, wherein r is an integer from 1 to 10, preferably n is an integer from 1 to 5, such as 1 to 4, or 1, 2, 3, 4, or 5.

The detecting agent and/or photosensitizing agent can be reacted with a biomolecule or a carrier molecule using conjugation chemistry well known in the art. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a linker with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

When linking a biomolecule having a carboxylic acid group for attachment to an amine containing molecule, the carboxylic acid can first be converted to a more reactive form using an activating reagent, to form for example, a N-hydroxy succinimide (NHS) ester or a mixed anhydride. The amine-containing metabolite is treated with the resulting activated acid to form an amide linkage. One of skill in the art will recognize that alternatively, the NHS ester can be on the metabolite and the amine can be on the carrier protein.

In other embodiments, the linker is a member selected from the group of a PEG, a block copolymer of PEG-polyurethane and a PEG-polypropylene. In yet other embodiments, the linker is a member selected from the group of a polysaccharide, a polypeptide, an oligosaccharide, a polymer, a co-polymer and an oligonucleotide.

The linker can have the formula:

$$-X^1-Y^1-X^2-$$

wherein: $X^1$ is a member selected from the group of a bivalent radical, a direct link, oxygen, an optionally substituted nitrogen and sulfur; $Y^1$ is a member selected from the group of a direct link and $C_1$-$C_{10}$ alkylene optionally interrupted by a heteroatom; and $X^2$ is a member selected from the group of a bivalent radical, a direct link, oxygen, an optionally substituted nitrogen and sulfur.

Preferably, the bivalent radical of $X^1$ and $X^2$ are each independently selected from the group of a direct link, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

Alternatively, the linker is $-(CH_2)_r-$, wherein r is an integer from 1 to 50.

Selected example of reactive functionalities useful for the attaching of the agent to the nanocarriers or biomolecule are shown in Table 1, wherein the bond results from the reaction of an agent (e.g., detecting agent or photosensitizing agent) with the nanocarriers or biomolecule. Those of skill in the art will know of other bonds suitable for use in the present invention.

TABLE 1

| A<br>Reactive functionality (either on the agent or the nanocarrier/biomolecule) | B<br>Complementary group (either on the nanocarrier/ biomolecule or the agent) | C<br>The resulting bond |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| activated carboxylic acids | amines/anilines | carboxamides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —COM, where M is a good leaving group (e.g. succinimidyloxy (—OC$_4$H$_4$O$_2$) sulfosuccinimidyloxy (—OC$_4$H$_3$O$_2$SO$_3$H), -1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

In some embodiments, the covalent linkage between the linker and biomolecule is selected from the group consisting of a direct bond, an amide bond, an ester bond, an ether bond, an oxime bond, a phosphate ester bond, a sulfonamide bond, a thioether bond, a thiourea bond, and an urea bond.

G. Targeting Molecules

In certain embodiments, the external surface of the nanocarrier is attached to a 1) targeting molecule, as well as 2) a therapeutic agent and 3) a detecting agent. The targeting molecule can be entrapped within the particle, associated with the surface of the nanocarrier (e.g., adsorbed or conjugated (directly or indirectly) to the nanocarrier surface), and/or otherwise associated with the nanocarrier to varying degrees (e.g., admixed with nanocarrier in a liquid suspension, admixed with the nanocarrier in a solid composition, for instance, co-lyophilized with the nanocarrier, etc.), among other possibilities. In some embodiments, at least two different targeting molecules are attached to the nanocarrier.

In some embodiments, the targeting molecule specifically binds to an antigen such as a tumor antigen, bacterial antigen viral antigen, and fungal antigen. The targeting molecule can recognize tumor antigens such as, but not limited to: (a) cancer-testis antigens such as NY-ESO-1, SSX2. SCP1 as well as RAGE, BAGE, GAGE and MAGE family polypeptides, for example, GAGE-1, GAGE-2, MAGE-1. MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g. melanoma, pancreatic cancer and colorectal cancer), CDK4 (associated with, e.g. melanoma), MUM1 (associated with, e.g., melanoma), caspase-8 (associated with, e.g., head and neck cancer), CIA 0205 (associated with, e.g., bladder cancer), HLA-A2-R 1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, MA 0205, CDC-27, and LDLR-FUT. (c) over-expressed antigens, for example, Galectin 4 (associated with, e.g., colorectal cancer), galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g. renal cancer), aldolase A (associated with, e.g., lung cancer), PRAME (associated with, e.g. melanoma). HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g. prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, (CT7, 43-9F, 5T4, 791 Tgp72, beta-HCG, BCA225, BTAA, CA 125, CA 15-3 (CA 27.29\BCAA). CA 195, CA 242, CA-50, CAM43, CD68\KP1, CO-029, FGF-5, Ga733 (EpCAM), 1HTgp-175, M344, MA-50, MG7-Ag, MOV18, NB/70K, NY-CO-1. RCAS1, SDCCAG16, TA-90 (Mac-2 binding protein\cyclophilin C-associated protein), TAAL6, TAG72, TLP, TPS, and the like.

In some embodiments, the targeting molecule is an antibody that binds an antigen selected from the group consisting of, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen and a trophoblastic tumor cell surface antigen.

In some embodiments, targeting moiety is an antibody that binds an antigen selected from the group consisting of 5 alpha reductase, α-fetoprotein, AM-1, APC, APRIL, BAGE, β-catenin, Bcl2, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC27, CDK4, CEA, c-myc, Cox-2, DCC, DcR3, E6/E7, EGFR, EMBP, Ena78, FGF8b and FGF8a, FLK-1/KDR, folic acid receptor, G250, GAGE-Family, gastrin 17, GD2/GD3/GM2, GnRH, GnTV, gp100/Pme117, gp-100-in4, gp15, gp75/TRP-1, hCG, Heparanase, Her2/neu, HER3, Her4, HMTV, HLA-DR10, Hsp70, hTERT, IGFR1, IL-13R, iNOS, Ki 67, KIAA0205, K-ras, H-ras, N-ras, KSA, (CO17-1A), LDLR-FUT, MAGE Family (MAGE1, MAGE3, etc.), mammaglobin, MAP17, Melan-A/, MART-1, mesothelin, MIC A/B, MT-MMP's, such as MMP2, MMP3, MMPI, MMP9, Mox1, MUC-1, MUC-2, MUC-3, and MUC-4, MUM-1, NY-ESO-1, Osteonectin, p15, P170/MDR1, p53, p97/melanotransferrin, PAI-1, PDGF, plasminogen (uPA), PRAME, probasin, progenipoietin, PSA, PSM, RAGE-1, Rb, RCAS1, SART-1, SSX gene, family, STAT3, STn, TAG-72, TGF-α, TGF-β, and thymosin β, 15, nucleolin, Cal5-3, astro Intestinal Tumor Antigen (Ca19-9), ovarian tumor antigen (Ca125), tag72-4 antigen (CA72-4) and carcinoembryonic antigen (CEA).

In some embodiments, the targeting molecule is a carbohydrate. Carbohydrates may be natural or synthetic. A carbohydrate may be a derivatized natural carbohydrate. In some embodiments, the carbohydrate comprises monosaccharide or disaccharide, including but not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, or neuramic acid. In some embodiments, the carbohydrate is a polysaccharide, such as, but not limited to, pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In some embodiments, the carbohydrate is a sugar alcohol, such as, but not limited to mannitol, sorbitol, xylitol, erythritol, maltitol, or lactitol.

H. Diagnostic Uses

The probe can be combined with the sample in any way that facilitates contact between the probe and the sample of interest. The probe typically forms a covalent or non-covalent association or complex with an element of the sample, or is simply present within the bounds of the sample or portion of the sample. The sample is then illuminated at a wavelength selected to elicit the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are be excitable at or near the wavelengths 633-636 nm, 647 nm, 660 nm, 680 nm and beyond 700 nm, such as 780 nm, 810 nm and 850 nm as these regions closely match the output of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. In certain other aspects, the probes are used as in vivo optical imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. The probes of the present invention are particularly useful for imaging tumors, tissues, and organs in a subject. In one embodiment, the probes are useful for the detection of the presence of tumors and other abnormalities by monitoring the blood clearance profile of the dyes. In another embodiment, the probes are useful for laser assisted guided surgery for the detection of micrometastases of tumors upon laparoscopy.

The probes may be administered either systemically or locally to the organ or tissue to be imaged, prior to the imaging procedure. In one embodiment, the probes are administered intravenously. In another embodiment, the probes are administered parenterally. In yet another embodiment, the probes are administered enterally. The compositions used for administration of the probe typically contain an effective amount of the detecting agent along with conventional pharmaceutical carriers and excipients appropriate for the type of administration contemplated. For example, parenteral formulations advantageously contain a sterile aqueous solution or suspension of the dye compound or conjugate according to the invention. Compositions for enteral administration typically contain an effective amount of the dye in aqueous solution or suspension that may optionally include buffers, surfactants, thixotropic agents, flavoring agents, and the like.

The compositions can be administered in doses effective to achieve the desired optical image of a tumor, tissue, or organ. Such doses may vary widely, depending upon the particular dye compound or conjugate employed, the tumor, tissue, or organ subjected to the imaging procedure, the imaging equipment being used, and the like.

I. Therapeutic Uses

In yet other aspects, the present invention provides methods and compounds for photodynamic therapy (PDT) of target tumors, tissues, and organs in a subject. PDT is a two-step treatment process that may be used in a wide variety of cancers and diseased tissue and organs. The first step in this therapy is carried out by administering a photosensitizing agent systemically by ingestion or injection, or topically applying the compound to a specific treatment site on a subject, followed by illumination of the treatment site with light having a wavelength or waveband corresponding to a characteristic absorption waveband of the photosensitizing agent. The light activates the photosensitizing agent, causing singlet oxygen radicals and other reactive species to be generated, leading to a number of biological effects that destroy the abnormal or diseased tissue, which has absorbed the photosensitizing agent. The depth and volume of the cytotoxic effect on the abnormal tissue, such as a cancerous tumor, depend in part on the depth of the light penetration into the tissue, the photosensitizing agent concentration and its cellular distribution, and the availability of molecular oxygen, which will depend upon the vasculature system supplying the tumor, tissue, or organ.

In certain instances, the present invention provides methods for treatment, wherein for example, a tumor is treated using the therapeutic agent and thereafter, imaged to ascertain the extent of treatment. The treatment can be repeated until the tumor is destroyed or the site of treatment is satisfactorily complete. In certain instances, the methods include, injecting the probe or composition, treating the tumor using photodynamic therapy and thereafter imaging to ascertain the extent of treatment.

The method of the present invention provides for administering to the subject a therapeutically effective amount of a targeted photosensitizing agent, such as a therapeutic-diagnostic probe. The probe can be administered systemically by ingestion or injection, or locally administered to a target tissue site or to a surgical site. The photosensitizing agent of the probe can bind to one or more types of target cells or tissues, such as circulating tumor cells or cells of a solid tumor. When exposed to photoactivating light of an appropriate waveband, the agent absorbs the light, causing substances to be produced that impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

The probes and activating light can be administered by any means known in the art for PDT, including, but not limited to, ingestion, injection, transcutaneous administration, transdermal administration, and transillumination. Preferably, the light is administered transcutaneously to a subject. For example, "transcutaneous" as used herein refers to the passage of light through unbroken tissue. Where the tissue layer is skin or dermis, transcutaneous includes "transdermal" and it will be understood that the light source is external to the outer skin layer. However, the term "transillumination" as used herein refers to the passage of light through a tissue layer, such as the outer surface layer of an organ, e.g., the liver, and it will be apparent that the light source is external to the organ, but internal or implanted within the subject or patient.

In some embodiments, the forms of energy used for administering PDT include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Photosensitive agents typically have one or more absorption wavebands that excite them to produce the substances which damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins.

In further embodiments, the target tumor, tissue, or organ for treatment with PDT is selected from the group consisting of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, and diseased cells in which the disease is one of an autoimmune and an inflammatory disease. In yet a further embodiment, the target tissue is a lesion in the vascular system of a type selected from the group consisting of atherosclerotic lesions, arteriovenous malformations, aneurysms, and venous lesions.

IV. Examples

The following examples are offered to illustrate, but not to limit, the claimed invention.

Example 1. Therapeutic and Diagnostic Probes Containing a Viral Particle

This example provides an exemplary embodiment of a therapeutic and diagnostic probe as described herein.
Producing a Viral Particle Based Probe A recombinant DNA molecule containing a sequence encoding a papillomavirus L1 protein, a L2 protein or a combination of L1 and L2 proteins is constructed using standard molecular biology methods. See, for example, Sambrook et al., Molecular cloning: a laboratory manual, $3^{rd}$. ed., Cold Spring Harbor, N.Y., Cold Spring Harbor Laboratory. A host cell such as a bacterial cell is transfected with the recombinant DNA molecule. Thereafter, the L1 and L2 capsid proteins are purified from the transfected cells such that they self-assemble into papillomavirus-like particles. See, for example, U.S. Application Publication No. 2011/0091496. IRDye®800CW-n-hydroxysuccinimide (NHS) ester (LI-COR, Lincoln, Nebr.) and IRDye® 700DX-NHS ester are conjugated to the viral particle according to the manufacturer's instructions.
Using the Viral Particle Based Probe to Induce Cell Death of a Target Cell in a Subject The probe is injected intravenously into a subject, e.g., a human subject. NIR infrared fluorescence is visualized at different time points with an optical imager at excitation of 774 nm and emission at 789 nm. The non-invasive deep-tissue imaging allows the clinician to identify target cells, e.g., diseased cells, in various tissues of the body.

After the location of the probe is determined, an activating light is directed at the specific target cells bound to the probe. The photosensitizer agent of probe is exposed to the light, thereby generating a cytotoxic singlet oxygen. This, in turn, results in cell death of the target cell via apoptosis and/or necrosis.

Example 2. Therapeutic and Diagnostic Probes Containing a Viral Particle and a Targeting Moiety This example provides an exemplary embodiment of the present invention, in particular, a therapeutic and diagnostic probe based on a viral particle that selectively binds to EGFR expressing cells, such as cancer cells.

The virus-like particle based probe is generated according to the method described in Example 1 with modifications to express a targeting moiety, such as EGF on the surface of the probe. The EGF protein can be labeled on free amine groups using an NHS ester derivative of IRDye® 700DX or IRDye® 800CW (LI-COR, Lincoln, Nebr.). The viral-like particle can also be linked to the dye(s) through a linker as described above.

The probe is administered to the subject, e.g., the human subject, by intravenous injection or by direct injection into a solid tumor containing EGFR-overexpressing cells. The EGF probe then binds to EGFR on the surface of cancer cells. Near-infrared fluorescence imaging is performed at various time points to determine the location of the IRDye®800CW dye of probe. An activating light is directed to the IRDye® 700DX of the probe which in turn produces a cytotoxic singlet oxygen that induces cell death in the EGFR-overexpressing cancer cells.

In summary, this example illustrates the use of a therapeutic-diagnostic probe that contains an EGF targeting moiety that selectively binds to EGFR expressing cells. Described herein is a method for inducing cell death of EGFR expressing cancer cells by administering the probe.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A probe comprising a nanocarrier attached to both (1) an imaging agent, wherein the imaging agent is a cyanine dye; and (2) a therapeutic agent, which is IRDYE700DX, wherein said nanocarrier is an antibody or a fragment thereof.

2. The probe of claim 1, wherein said therapeutic agent is attached to said nanocarrier via a first linker.

3. The probe of claim 2, wherein said imaging agent is attached to said nanocarrier via a second linker.

4. A method for detecting a target cell in an individual, said method comprising:
   (a) contacting said target cell with a probe comprising a nanocarrier attached to both (1) an imaging agent, which imaging agent is a cyanine dye; and (2) a therapeutic agent, wherein the therapeutic agent is IRDYE700DX, wherein the probe selectively associates with the said target cell, wherein said nanocarrier is an antibody or fragment thereof; and
   (b) detecting said imaging agent thereby providing an indication of the presence and/or location of said target cell in the individual.

5. The method of claim 4, wherein said contacting comprises systemic administration to the individual, local administration to a tumor, or administration to a surgical site.

6. The method of claim 4, wherein said target cell is a cell of a solid tumor.

7. The method claim 4, further comprising exposing said therapeutic agent to a photoactivating light, thereby inducing apoptosis and/or necrosis of said target cell in the individual.

8. A method for inducing cell death in a target cell in an individual, said method comprising:
 (a) contacting said target cell with a probe comprising a nanocarrier attached to both (1) an imaging agent, which imaging agent is a cyanine dye; and (2) a therapeutic agent, wherein the therapeutic agent is IRDYE700DX, wherein the probe selectively associates with said target cell, wherein said nanocarrier is an antibody or fragment thereof; and
 (b) exposing said therapeutic agent to a photoactivating light, thereby inducing apoptosis and/or necrosis of said target cell in the individual.

9. The method of claim 8, wherein said contacting comprises systemic administration to the individual, local administration to a tumor, or administration to a surgical site.

\* \* \* \* \*